(12) United States Patent
Schmidt

(10) Patent No.: US 8,242,320 B2
(45) Date of Patent: Aug. 14, 2012

(54) CUMENE PRODUCTION WITH HIGH SELECTIVITY

(75) Inventor: Robert J. Schmidt, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 192 days.

(21) Appl. No.: 12/751,132

(22) Filed: Mar. 31, 2010

(65) Prior Publication Data

US 2011/0245558 A1 Oct. 6, 2011

(51) Int. Cl.
*C07C 2/66* (2006.01)
(52) U.S. Cl. .................................................. 585/467
(58) Field of Classification Search .................. 585/467
See application file for complete search history.

(56) References Cited

U.S. PATENT DOCUMENTS

| | | | | |
|---|---|---|---|---|
| 4,870,222 | A | * | 9/1989 | Bakas et al. ................... 585/323 |
| 5,522,984 | A | * | 6/1996 | Gajda et al. .............. 208/120.01 |
| 6,005,152 | A | | 12/1999 | Amarilli et al. |
| 6,008,422 | A | | 12/1999 | Schulz et al. |
| 6,339,179 | B1 | | 1/2002 | Schulz |
| 6,440,886 | B1 | | 8/2002 | Gajda et al. |
| 6,756,030 | B1 | | 6/2004 | Jan et al. |
| 6,878,654 | B2 | | 4/2005 | Dandekar et al. |
| 7,091,390 | B2 | | 8/2006 | Jan et al. |
| 7,268,267 | B2 | | 9/2007 | Jan et al. |
| 7,420,098 | B2 | | 9/2008 | Schmidt |
| 7,498,471 | B2 | | 3/2009 | Schultz |
| 7,566,429 | B2 | | 7/2009 | Buelna et al. |
| 7,638,667 | B2 | | 12/2009 | Jan et al. |
| 2004/0182744 | A1 | | 9/2004 | Jan et al. |
| 2004/0199036 | A1 | * | 10/2004 | Jan et al. ........................ 585/467 |
| 2006/0159615 | A1 | | 7/2006 | Jan et al. |
| 2008/0171902 | A1 | | 7/2008 | Jan et al. |
| 2010/0012552 | A1 | | 1/2010 | James, Jr. et al. |
| 2010/0056837 | A1 | | 3/2010 | Jan et al. |

OTHER PUBLICATIONS

Kaeding et al., "Shape-selective reactions with zeolite catalysts—6. alkylation of benzene with propylene to produce cumene," J. Catal. (ISSN 0021-0517) V109 N.1 212-16 (Jan. 1988) Academic Press.
Pradhan et al., "Isopropylation of benzene over EU-1 zeolite catalyst," Applied Catalysis (ISSN 0166-9834) V72 N.2 311-19 (May 16, 1991) Elsevier.
Buelna et al., "A one-step catalytic separation process for the production of cumene," Catalysis Letters, v 102, n 3-4, p. 285-288, Aug. 2005.

* cited by examiner

*Primary Examiner* — Thuan Dinh Dang
(74) *Attorney, Agent, or Firm* — Mark R Willis

(57) ABSTRACT

Cumene production methods are disclosed, based on the alkylation of benzene with propylene, in which byproducts of the alkylation reaction are advantageously reduced to achieve a high cumene selectivity. This may be attained by (i) reducing the portion of the total alkylation effluent that is recycled, after cooling, to the alkylation reaction zone for quenching or direct heat exchange and/or (ii) reducing the benzene:propylene molar ratio of the alkylation feedstock. To manage the temperature differential across catalyst bed(s) in the alkylation reaction zone, indirect heat exchange may be used to remove heat.

6 Claims, 4 Drawing Sheets

CUMENE PRODUCTION WITH HIGH SELECTIVITY

FIELD OF THE INVENTION

The present invention relates to methods for cumene production from the alkylation of benzene with propylene, and particularly those in which cumene selectivity is increased through lower effluent recycle ratios returned, and/or lower molar excesses of benzene fed, to the alkylation reaction zone.

DESCRIPTION OF RELATED ART

The alkylation of aromatic substrates with olefins to produce monoalkyl aromatics is a well developed art that is practiced industrially on a large scale. One commercial application is the alkylation of benzene with propylene to produce cumene (isopropylbenzene), which is subsequently used in the manufacture of phenol and acetone via the air oxidation of cumene and subsequent acid-catalyzed decomposition of the intermediate hydroperoxide. Invariably, the production of the desired, monoalkylated product cumene is accompanied by the formation of undesired polyalkylated aromatic byproducts, notably the dialkylated byproduct diisopropylbenzene (DIPB) and trialkylated byproduct triisopropylbenzene (TIPB).

These polyalkylated aromatic compound byproducts therefore represent a reduction in the efficient use of the aromatic substrate, benzene, and olefin, propylene, in the alkylation reaction zone. The costs associated with the losses in cumene product yield, due to the non-selective polyalkylated aromatic compound formation, can be at least partially offset by transalkylating these byproducts, in a separate transalkylation reaction zone, with benzene in the presence of a suitable transalkylation catalyst. For example, one mole of each of DIPB and benzene can transalkylate to yield an additional two moles of cumene product. So-called combination processes, involving alkylation that is integrated with transalkylation, can therefore significantly improve the yield of the desired monoalkylated aromatic compound (e.g., cumene).

Even so, however, the utility and equipment costs associated with (i) separation of non-selective byproducts from the alkylation effluent and (ii) further reaction of these byproducts in a catalytic transalkylation reaction zone are substantial. A common way to reduce these costs associated with byproduct handling and conversion involves using a common product separation (recovery) section for both the alkylation and transalkylation effluent streams, optionally after removing light components such as propane from one or both of these effluents by fractionation. The same distillation columns and other equipment can therefore be used to recover the cumene product, separate from a heavy byproduct containing polyalkylated aromatic compounds, in addition to (i) a fraction rich in DIPB and TIPB that is fed to the transalkylation reaction zone and (ii) unreacted benzene that is recycled to both the alkylation and transalkylation reaction zones. The relatively minor heavy byproducts, which are mostly (i) aromatic compounds including polyalkylated aromatics boiling above the boiling point of TIPB, as well as (ii) other higher boiling byproducts of either reaction zone (e.g., diphenylalkanes), are normally removed as a high boiling (e.g., bottoms) fraction from a distillation column generally referred to as the DIPB column. This column is conventionally operated under subatmospheric (vacuum) pressure, in an effort to distill, without using excessive reboiler temperatures, TIPB together with DIPB into a low boiling fraction that, when contacted in the transalkylation reaction zone with benzene, can advantageously produce additional cumene from both of these compounds.

Thus, in a representative integrated aromatic alkylation process for producing cumene, benzene and propylene are charged into an alkylation reaction zone comprising one or more reactors containing alkylation catalyst, or alternatively a single reactor comprising multiple beds of alkylation catalyst. A molar excess of benzene to propylene, for example in the range from about 4:1 to about 16:1, is normally maintained throughout the alkylation reaction zone to limit the concentration of the highly reactive olefin. Also, a considerable portion of the total alkylation effluent, after cooling, is recycled to the alkylation reaction zone as a heat sink to manage the high temperature differential from the inlet to the outlet of the reaction zone that would otherwise result from the highly exothermic alkylation reaction. The portion of the alkylation effluent that is not recycled is in some, but not all, cases sent to a depropanizer column for the removal, by distillation, of lower boiling components such as propane and water that may be present initially in the propylene feed. The depropanizer column bottoms is then combined with the effluent from the transalkylation reaction zone comprising a transalkylation catalyst. As discussed above, non-selective polyalkylated aromatic products of the alkylation reaction, namely DIPB and TIPB, are reacted with benzene in the transalkylation reaction zone to produce additional monoalkylated aromatic product, in this case cumene.

In this representative, integrated alkylation/transalkylation process for cumene production, the combined alkylation and transalkylation reaction zone effluents (optionally after removal of the lower boiling components from one or both of these effluents) are therefore sent to the same product separation section to recover benzene, cumene product, polyisopropylbenzene byproducts of the alkylation reaction zone (e.g., DIPB and TIPB), and heavier byproducts by distillation. Traditionally, three distillation columns are used for product recovery. The first is normally referred to as a benzene column, used to recover excess benzene from the reactor effluents in an overhead or lower boiling fraction. The recovered benzene is then recycled to the alkylation and transalkylation reaction zones to satisfy some or all of the benzene needed to obtain the desired benzene:olefin ratio in each zone. The second distillation column is normally referred to as a cumene column, the feed to which is generally the bottoms or a higher boiling fraction of the upstream benzene column. The cumene product is often taken as a net overhead or low boiling fraction from the cumene column. The cumene product may then be used in downstream applications such as phenol or acetone production processes, or otherwise may be sent to storage. The third distillation column is the DIPB column discussed above, the feed to which is generally the bottoms or a higher boiling fraction of the upstream cumene column. As noted, the DIPB column is used to recover di and tri-alkylated aromatic compounds in an overhead or lower boiling fraction and recycle these to the transalkylation reaction zone. The collective heavier products, removed as a bottoms or higher boiling fraction of this column, may be cooled and sent to storage.

In cumene production processes described above, the per-pass conversion of the limiting olefinic reagent propylene, is generally complete or substantially complete in the alkylation reaction zone. Therefore, an overriding objective, which governs process economics, is achieving a high selectivity to the desired cumene product, in order to reduce the quantity of recycled DIPB and TIPB byproducts and the capacity of the transalkylation reaction zone required for their further conversion. Various alkylaromatic production processes and catalysts used in these processes, along with their associated advantages are described, for example, in U.S. Pat. Nos. 7,498,471; 6,440,886; 6,339,179; and US 2008/0171902. Improvements that relate to reducing byproduct formation in the production of cumene are continually being sought. Those skilled in the art recognize the significant commercial impact of even a modest improvement in product selectivity.

SUMMARY OF THE INVENTION

The present invention is associated with the discovery of cumene production methods, based on the alkylation of benzene with propylene, in which byproducts of the alkylation reaction are advantageously reduced to achieve a high selectivity, for example at least about 85% on a molar basis, of the total converted products cumene and its dialkylated and trialkylated derivative byproducts (i.e., diisopropylbenzene (DIPB) and triisopropylbenzene (TIPB)), to the desired product cumene. For purposes of this disclosure, therefore, "selectivity" means the ratio of moles of cumene:moles of total (cumene+DIPB+TIPB) in the alkylation effluent or product from the alkylation reaction zone. Moreover, it has also been determined that, according to particular embodiments, this high cumene selectivity is achieved using an economically benzene:propylene molar ratio of the alkylation feedstock, for example at most about 2.5:1. The selectivity improvement is associated with a number of advantages, in terms of process economics, related to reduced operating and equipment costs for recycling, converting, and/or separating undesired byproducts. These and other process features are beneficially combined with particular alkylation catalyst systems, and particularly catalysts having a framework $Si/Al_2$ molar ratio in the range from about 24 to about 35.

High selectivity may be attained by reducing the portion of the total alkylation effluent that is recycled, after cooling, to the alkylation reaction zone as a heat sink to manage the temperature differential across the alkylation reaction zone or across individual alkylation catalyst beds within this zone. Reducing the recycle ratio in the alkylation reaction zone can beneficially prevent the re-introduction of at least some of the cumene into a reaction environment that promotes its further alkylation to non-selective byproducts such as diisopropylbenzene (DIPB) and triisopropylbenzene (TIPB). Thus, while effluent recycle is conventionally used to limit the maximum alkylation reaction zone temperature and consequently the rates of non-selective reactions (e.g., to produce normal-propylbenzene (NPB) and ethylbenzene (EB) byproducts), this benefit is achieved at the expense of obtaining an alkylation effluent comprising cumene at well below the equilibrium level of a cumene/DIPB/TIPB mixture under the alkylation reaction zone conditions.

Aspects of the invention therefore relate to the improved cumene selectivity, in the alkylation of benzene with propylene, attained by reducing or even eliminating the recycle of a portion of the alkylation effluent back to the alkylation reaction zone. According to some embodiments, the increased temperature differential (ΔT) across one or more alkylation catalyst beds of the alkylation reaction zone (e.g., the beds being contained within an alkylation reactor or within separate reactors), as a result of reducing or eliminating alkylation effluent recycle, may be at least partially offset by removing heat from the reaction zone by indirect heat exchange. For example, heat may be exchanged between an alkylation catalyst bed effluent and a cooling medium (e.g., water), such that the resulting cooled alkylation catalyst bed effluent is fed to a downstream alkylation catalyst bed (e.g., an immediately adjacent downstream catalyst bed in series with the bed from which the alkylation catalyst bed effluent is removed for indirect heat exchange) that is also within the alkylation reaction zone. The removed heat can therefore beneficially be recovered as steam (e.g., medium pressure steam).

Other aspects of the invention relate to improvements in cumene selectivity resulting from reducing the benzene:propylene molar ratio of the alkylation feedstock entering the alkylation reaction zone (e.g., entering an alkylation reactor at multiple locations corresponding to inlets of multiple beds of alkylation catalyst). Especially surprising is that a combination of a reduced benzene:propylene molar ratio (e.g., at most about 2.5:1) and a reduced alkylation effluent recycle ratio (e.g., at most about 3:1) can result in a dramatic improvement in cumene selectivity in the alkylation reaction zone, with an exemplary selectivity being greater than about 85%, typically greater than about 88%, and often being greater than about 90%, by weight.

These process parameters are advantageously combined with particular catalyst systems, in the alkylation reaction zone, to achieve the performance advantages noted above, particularly with respect to the high cumene selectivity. Alkylation catalysts that have now been demonstrated to perform exceptionally well in conjunction with the alkylation effluent recycle ratios and/or feedstock reactant ratios described above include those comprising UZM-8 zeolite, and particularly comprising this zeolite having a high having a framework $Si/Al_2$ (or silica to alumina) molar ratio, for example from about 24 to about 35. When used in the alkylation reaction zone (e.g., in multiple alkylation catalyst beds configured in series within this zone), catalysts comprising this zeolite have been shown to tolerate not only the higher temperature differences across one or more beds of this alkylation catalyst as a result of reducing the alkylation effluent recycle ratio, but also the higher olefin concentrations to which this alkylation catalyst is exposed as a result of reducing the feedstock benzene:propylene molar ratio. Normally, in view of the poorer performance that is often observed with conventional alkylation catalysts, either of these effects would be expected to cause excess catalyst deactivation and/or byproduct formation.

Further aspects of the invention relate to the discovery of operational synergy between the alkylation reaction zone, with the high cumene selectivities as discussed above, and the transalkylation reaction zone and/or product recovery section that results in overall significantly improved process economics. Advantageously, high cumene selectivity in the alkylation reaction zone (e.g., greater than about 88%), and especially at particular benzene:propylene molar ratios of the alkylation feedstock (e.g., from about 2.2 to about 3.0), can decrease the yield loss of net benzene and propylene that are converted to TIPB and higher molecular weight byproduct compounds to generally less than 1%. At sufficiently low production of TIPB, the conventional distilling, in the product recovery section, of the higher boiling byproduct fraction (obtained from recovering cumene product as a lower boiling fraction) can be carried out (e.g., in the DIPB column) at atmospheric pressure or above, rather than under vacuum pressure as performed conventionally to recover TIPB together with DIPB in the lower boiling (e.g., overhead) fraction that is fed back to the transalkylation reaction zone.

According to embodiments of the invention, therefore, the yield loss of TIPB may be reduced to an extent that the cost savings associated with operating distillation in the DIPB column at atmospheric pressure or above, rather than under vacuum pressure, surpass the relatively smaller expenses associated with removing the TIPB byproduct, rather than recycling this compound to the transalkylation reaction zone for production of additional cumene. According to other embodiments that exploit high cumene selectivity and particularly the low net production of TIPB in the alkylation reaction zone, the transalkylation catalyst advantageously comprises beta zeolite that, unlike conventional transalkylation catalysts, does not require the presence of TIPB in the transalkylation reaction zone to prevent a net production of this compound. Importantly, beta zeolite is shape selective and can therefore be used in a transalkylation reaction zone operating at a DIPB conversion of at least about 60%, compared to conventional conversion levels of only 50-60%, without a significant production of transalkylation byproducts such as normal-propylbenzene (NPB) and ethylbenzene.

These and other aspects and features relating to the present invention are apparent from the following Detailed Description.

BRIEF DESCRIPTION OF THE DRAWINGS

FIG. 1 is to be understood to present an illustration of the invention and/or principles involved. Details including pumps, compressors, instrumentation, and other items not essential to the understanding of the invention are not shown. As is readily apparent to one of skill in the art having knowledge of the present disclosure, methods for producing cumene and particularly at high selectivity in the alkylation reaction zone (to optionally achieve operational synergy with the integrated transalkylation reaction zone as described herein), according to various other embodiments of the invention, will have configurations and components determined, in part, by their specific use.

In FIGS. 2-4, the "UZM-8HR catalyst" comprised UZM-8 zeolite having a framework $Si/Al_2$ molar ratio in the range of 24-35, whereas the "UZM-8 catalyst" comprised UZM-8 zeolite having a framework $Si/Al_2$ molar ratio in the range of 19-21.

DETAILED DESCRIPTION

Figure 1:
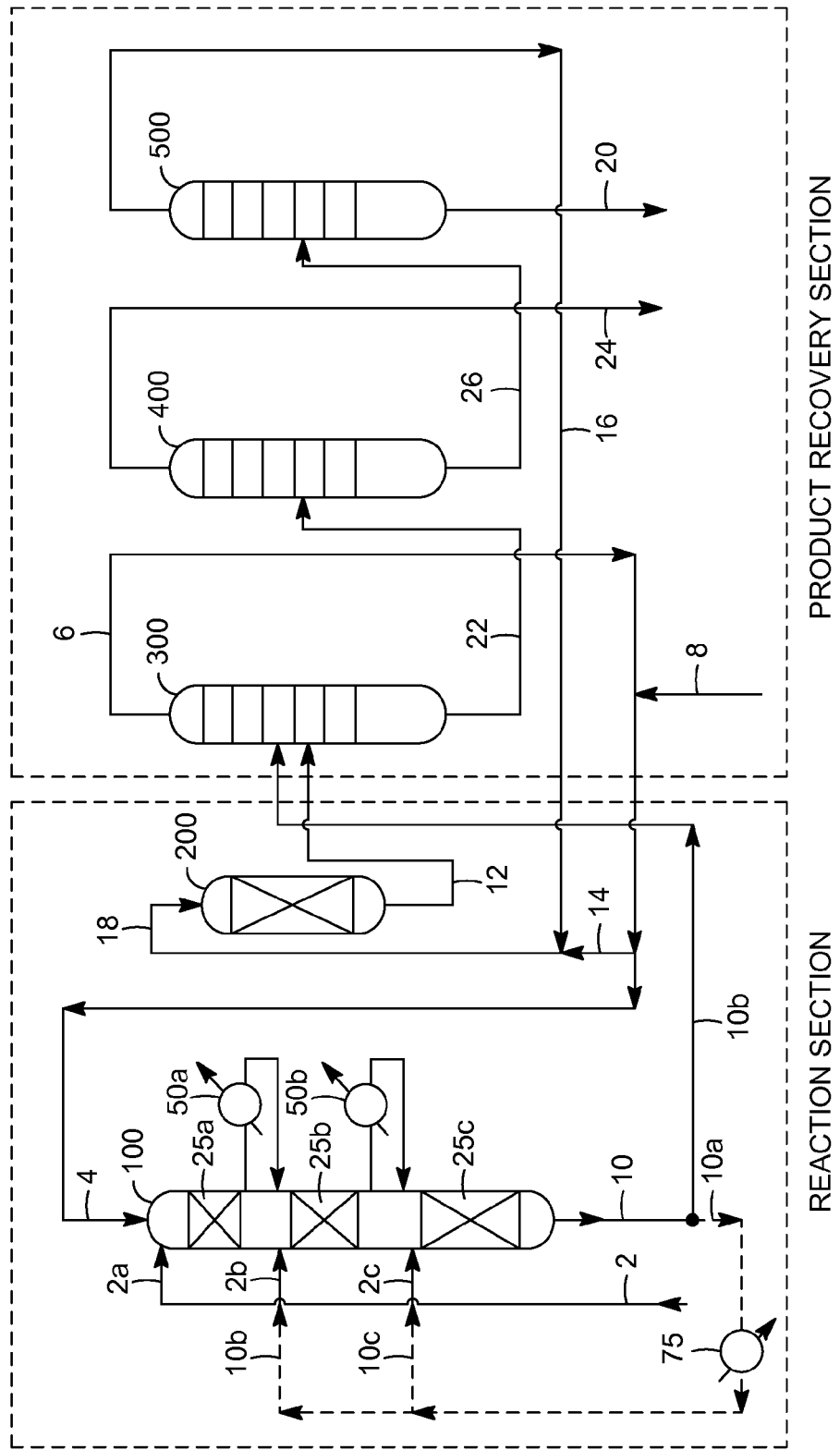
FIG. 1 depicts a representative cumene production process, in which heat is removed from the alkylation reaction zone, namely by indirect heat exchange between pairs of adjacent alkylation catalyst beds in series.

The present invention relates to methods for producing cumene. Representative methods comprise flowing an alkylation feedstock comprising benzene and propylene to an alkylation reaction zone and withdrawing from this zone an alkylation effluent comprising cumene. As discussed above, the selectivity of the converted products of the alkylation reaction zone to cumene is generally at least about 80% (e.g., from about 80% to about 95%), typically at least about 85% (e.g., from about 85% to about 93%), and often at least about 88% (e.g., from about 88% to about 92%), on a molar basis as defined above. Selectivity may be increased by reducing the extent of (i) recycle of a portion of the alkylation effluent back to the alkylation reaction zone, and consequently (ii) further alkylation of cumene in the alkylation effluent to produce undesired diisopropylbenzene (DIPB) and triisopropylbenzene (TIPB) byproducts, in addition to other byproducts. Accordingly, in particular embodiments of the invention, a portion of the alkylation effluent exiting the alkylation reaction zone is recycled to this zone at a relatively low (compared to conventional cumene production processes) alkylation effluent recycle ratio (or recycle to feedstock ratio). Representative alkylation effluent recycle ratios, meaning ratios of the flow rate of the recycled portion of the alkylation effluent to the flow rate of the alkylation feedstock to the alkylation reaction zone, are generally less than about 4:1, typically less than about 3:1, and often less than about 2.5:1 (e.g., in the range from about 1:1 to about 2.5:1), by weight. The alkylation feedstock includes all benzene- and propylene-containing feeds entering the alkylation reaction zone, excluding the recycled portion of the alkylation effluent.

Temperature differences generally arise across the alkylation reaction zone, or across individual catalyst beds within this zone, as a result of the exothermic alkylation reaction that normally converts all or substantially all (e.g., at least about 99%, or at least about 99.5%) of the limiting reagent propylene in this reaction zone. Because higher recycle ratios are used in conventional processes to limit the temperature rise across this reaction zone, or across individual alkylation catalyst beds (i.e., from the inlet to the outlet of the alkylation reaction zone or its alkylation catalyst beds), processes according to embodiments of he invention may be carried out at relatively high temperature differences (ΔT values or catalyst bed exotherms) across the alkylation reaction zone or alkylation catalyst bed(s). For example, using the lower alkylation effluent recycle ratios discussed above, a representative temperature difference, in the case of an alkylation reaction zone comprising multiple alkylation catalyst beds in series, is generally from about 15° C. (27° F.) to about 45° C. (81° F.), and often from about 20° C. (36° F.) to about 40° C. (72° F.). These ranges of temperature differences generally apply to at least one alkylation catalyst bed within the alkylation reaction zone, although in many cases all of the beds are operated with approximately equal temperature differences within these ranges. The temperature difference may be controlled across each individual bed, in the case of an alkylation reaction zone comprising multiple alkylation catalyst beds in series, by dividing the flow of the recycled portion of the alkylation effluent among locations in the alkylation reaction zone. Often, these locations are between adjacent catalyst beds disposed in series in an alkylation reactor.

Cooling the portion of the alkylation effluent that is recycled, and introducing this recycled portion back into the alkylation reaction zone therefore limits the temperature difference across (i.e., quenches) the alkylation reaction zone and/or alkylation catalyst beds within this zone, by direct heat exchange with the reaction mixture at locations where the recycled portion is introduced. Direct heat exchange may also occur with portions of the alkylation feedstock (e.g., fresh benzene, recycle benzene, and/or propylene) being divided among locations in the alkylation reaction zone (e.g., corresponding to those among which the recycled portion of the alkylation effluent is divided, as discussed above, and/or those from which heat is removed by indirect heat exchanged, as discussed below).

According to some embodiments, the recycled portion of the alkylation effluent may be eliminated, such that the recycle ratio is 0 and there is no direct heat exchange with this recycled portion. With all other process variables unchanged, this generally maximizes the temperature difference across the alkylation reaction zone or alkylation catalyst bed(s) within this zone, but may also maximize cumene selectivity depending on the alkylation catalyst and the process parameters. In embodiments where none of the alkylation effluent is recycled to the alkylation reaction zone, a representative temperature difference across one or more of the alkylation catalyst beds within this zone in series is generally from about 15° C. (27° F.) to about 60° C. (108° F.), and typically from about 30° C. (54° F.) to about 50° C. (90° F.).

Whether or not at least a portion of the alkylation effluent is recycled, the temperature difference across the alkylation reaction zone or across individual catalyst beds within this zone may also be controlled by indirect heat exchange to remove heat from the alkylation reaction zone. Heat removal by indirect heat exchange is preferred in embodiments in which alkylation effluent recycle is eliminated. If the alkylation reaction zone comprises multiple alkylation catalyst beds in series, for example, heat may be removed from between at least one pair of adjacent alkylation catalyst beds, and is often removed from between all pairs of adjacent catalyst alkylation beds. Therefore, in representative embodiments in which the alkylation reaction zone comprises at least three alkylation catalyst beds in series within a single alkylation reactor, heat may be removed by indirect heat exchange from between at least each of both pairs of adjacent beds of the at least three alkylation catalyst beds, namely from between (i) a first, upstream bed and a second, intermediate bed and between (ii) the second, intermediate bed and a third, downstream bed. Locations of heat removal by indirect heat exchange (e.g., at differing axial positions (heights) along the length of a vertically oriented, cylindrical alkylation reactor, may therefore correspond to some or all of the locations discussed above, among which the recycled portion of the alkylation effluent (if used) is divided to quench the alkylation catalyst beds by limiting their temperature rise. In other embodiments, heat may be removed by indirect heat exchange between some pairs of adjacent alkylation catalyst beds while direct heat exchange (quenching) may be used between other pairs. For example, direct and indirect heat exchange may alternate between alternating pairs of adjacent alkylation catalyst beds.

Regardless of the particular configuration for interbed heat removal and/or quenching, any number of cooling media may be used for indirect heat exchange, including any process stream that could benefit from being heated indirectly against the effluent from an alkylation catalyst bed. A common cooling medium is water that, after exchanging heat with an alkylation catalyst bed effluent, can produce more valuable steam, for example medium pressure steam.

The lower recycle ratios and correspondingly high alkylation reaction zone or alkylation catalyst bed temperature differences, associated with processes described herein for the alkylation of benzene with propylene with a high selectivity to cumene, are advantageously used with alkylation catalysts found to exhibit good performance, in terms of activity, selectivity, and stability, even with these process parameters that are generally expected to provide a more severe operating environment. A further operating condition that improves cumene selectivity and that, although more severe, is well tolerated by preferred alkylation catalysts, is a reduction in the molar benzene:propylene molar ratio in the alkylation feedstock to the alkylation reaction zone. The alkylation feedstock includes all benzene- and propylene-containing feeds entering the alkylation reaction zone, but does not include the recycled portion (if any) of the alkylation effluent. The alkylation feedstock may therefore be, in a representative embodiment, a combined flow of propylene and fresh and/or recycle benzene feeds to a multibed alkylation reactor.

As discussed previously, conventional cumene production processes operate with a significant molar excess of benzene relative to propylene in the alkylation feedstock, such that the excess benzene provides, together with the recycled portion of the alkylation effluent, an additional heat sink. Also, the excess benzene dilutes the reactive olefin propylene to decrease the potential for polymerization and catalyst coking, resulting from the reaction of propylene with itself under alkylation reaction conditions. However, according to particular embodiments of the invention as described herein, the benzene:propylene molar ratio may be reduced to a value closer to its stoichiometric reaction ratio (1:1) for improved reactant utilization efficiency and/or further improved selectivity. Representative benzene:propylene molar ratios of the alkylation feedstock are generally at most about 3:1 (e.g., in the range from about 1:1 to about 3:1) and typically at most about 2.5:1 (e.g., in the range from about 1.5:1 to about 2.5:1), and often at most about 2:1 (e.g., in the range from about 1.5:1 to about 2:1).

A representative alkylation catalyst, which has been found to perform exceptionally well in cumene production processes utilizing one or more of the process parameters, including the alkylation effluent recycle ratios, direct and/or indirect heat exchange strategies, and/or benzene:propylene alkylation feedstock ratios discussed above, all of which individually or in combination may contribute to improvements in cumene selectivity, comprises UZM-8 zeolite. This zeolite is described in U.S. Pat. No. 6,756,030. The UZM-8 zeolite is generally present in an amount of at least 50% by weight, and often in an amount of at least 70% by weight, of the total catalyst weight, with the balance in most cases being a refractory inorganic oxide binder. A preferred binder is alumina, with gamma-alumina, eta-alumina, and mixtures thereof being particularly preferred. In exemplary embodiments, the UZM-8 zeolite is used in pure form without any binder. Under various processing conditions as discussed herein, it has been found that the atomic $Si/Al_2$ framework molar ratio of UZM-8 can be an important parameter in achieving the desirable cumene selectivity values (e.g., greater than about 85%) as discussed above. Especially advantageous results may be achieved, for example, using an alkylation catalyst comprising or consisting essentially of (e.g., in pure form without added binder) UZM-8 zeolite having a framework $Si/Al_2$ molar ratio from about 24 to about 35, and often from about 27 to about 33. As is understood in the art, the framework $Si/Al_2$ ratio is equivalent to the framework molecular silica to alumina ($SiO_2/Al_2O_3$) molar ratio, both of which are exactly twice the atomic Si/Al ratio.

A representative transalkylation catalyst found to perform exceptionally well in cumene production processes described herein with high cumene selectivity comprises beta zeolite, Y zeolite, or UZM-8 zeolite. A type of Y zeolite for use as an alkylation catalyst has a non-$H^+$ cation content of the zeolite Y of less than 200 ppm by weight, calculated as $NH_3$ equivalents. A preferred Y zeolite is a modified Y zeolite known as Y-85 and described in US 2008/0171902, hereby incorporated by reference. Beta zeolite is described in U.S. Pat. Nos.

4,891,458 and 5,081,323. Surface-modified beta zeolite, as described in U.S. Pat. No. 5,723,710, is an exemplary beta zeolite suitable as an alkylation catalyst. In any zeolitic alkylation catalyst, the zeolite is generally present in an amount of at least 50% by weight, and often in an amount of at least 70% by weight, of the total catalyst weight, with the balance in most cases being a refractory inorganic oxide binder. A preferred binder is alumina, with gamma-alumina, eta-alumina, and mixtures thereof being particularly preferred. A representative zeolitic alkylation catalyst comprises Y zeolite and an alumina or silica binder. Another comprises beta zeolite and an alumina or silica binder. In general, the zeolites described above are also suitable for use as transalkylation catalysts in integrated alkylation reaction zone/transalkylation reaction zone processes as described herein.

More generally, the catalysts used for alkylation and transalkylation generally comprise one of a class of aluminosilicate molecular sieves known as zeolites. Suitable zeolitic molecular sieves are crystalline aluminosilicates which in the calcined form may be represented by the general formula:

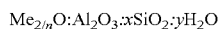

$Me_{2/n}O:Al_2O_3:xSiO_2:yH_2O$ where Me is a cation, n is the valence of the cation, x has a value of from about 5 to 100, and y has a value of from about 2 to 10. Zeolites are described in detail by D. W. Breck, *Zeolite Molecular Sieves*, John Wiley and Sons, New York (1974), and elsewhere. Suitable zeolites include Y zeolite, beta zeolite, X zeolite, mordenite, faujasite, zeolite omega, UZM-8, ZSM-5, PSH-3, MCM-22, MCM-36, MCM-49, and MCM-56. One or more types of zeolitic alkylation and/or transalkylation catalyst may be used in different catalyst beds in either of the different reaction (i.e., alkylation and transalkylation) zones.

An illustrative embodiment of a cumene production process is shown in the FIG. 1. According to this embodiment, an alkylation feedstock comprising propylene 2 and recycle alkylation benzene 4 is introduced to an alkylation reaction zone, namely alkylation reactor 100. Recycle alkylation benzene 4 comprises a portion of a lower boiling benzene fraction 6 recovered in the product recovery section and a portion of fresh benzene 8 added to the process. As shown, alkylation reactor 100 contains three alkylation catalyst beds (25a, 25b, 25c) in series and the flow of propylene 2 is divided among locations (2a, 2b, 2c) that are (i) upstream (above) the first upstream alkylation catalyst bed 25a, (ii) between the first, upstream alkylation catalyst bed 25a and the second, intermediate bed 25b, and (iii) between the second, intermediate bed 25b and a third, downstream bed 25c. Representative conditions in alkylation reactor 100 include a temperature from about from about 75° C. (167° F.) to about 250° C. (482° F.), a pressure from about 15 barg (218 psig) to about 65 barg (943 psig), and a weight hourly space velocity based on propylene (propylene WHSV) from about 0.1 hr$^{-1}$ to about 5 hr$^{-1}$. As is understood in the art, the propylene WHSV is the weight flow of propylene to the alkylation reaction zone divided by the total weight of the catalyst in this zone and represents the equivalent catalyst weight of propylene processed every hour.

The exothermic alkylation reaction causes a temperature rise across each of alkylation catalyst beds (25a, 25b, 25c), with representative temperature differentials as discussed above. The temperature rise across, and consequently the maximum bed temperature for, each of alkylation catalyst beds (25a, 25b, 25c) is limited in part by indirect heat exchange to remove heat from between both pairs of adjacent alkylation catalyst beds (25a/25b and 25b/25c). In particular, heat from effluents of the upstream 25a and intermediate 25b alkylation catalyst beds 25a, 25b is exchanged against a cooling medium (e.g., water) using coolers 50a, 50b, to heat the cooling medium, for example for generating steam (e.g., medium pressure steam) or otherwise for heating a process stream in the cumene production process of another process.

In combination with indirect heat exchange, direct heat exchange between propylene entering alkylation reaction zone 100 at locations 2b and 2c and the reaction mixture further helps limit the temperature across the alkylation catalyst beds. In optional embodiments (shown with broken arrows) in which a portion 10a of alkylation effluent 10 is cooled using cooler 75 and recycled to alkylation reaction zone 100, this recycled portion 10a may be divided among locations 10b, 10c between pairs of adjacent catalyst beds (25a/25b and 25b/25c), as discussed above, which correspond to locations of heat removal by indirect heat exchange and/or quenching by direct heat exchange. It will be appreciated, in view of the present specification, that any number of combinations of direct and/or indirect heat exchange, or alternatively either direct or indirect heat exchange alone, may be effective in limiting the temperature rise across one or more alkylation catalyst bed(s) to a desired degree. Processes described herein benefit generally from reducing or eliminating the recycle ratio back to the alkylation reaction zone 100 to improve cumene selectivity in this zone. Therefore, indirect heat exchange is often preferred, either alone or in combination with direct heat exchange, in view of the reduced capacity for direct heat exchange (quenching) with the alkylation effluent recycle according to various embodiments described herein.

All of alkylation effluent 10, or at least a non-recycled portion 10b of alkylation effluent 10 is fed, optionally following fractionation (not shown) to remove light components (e.g., propane), together with transalkylation effluent 12 of transalkylation reaction zone 200, to a product recovery section comprising multiple fractionation (distillation) columns. The product recovery section is typically used to recover, from at least the non-recycled portion 10b of the alkylation effluent and transalkylation effluent 12, a cumene product, a heavy byproduct, a benzene fraction, and a diisopropylbenzene (DIPB) fraction.

According to the illustrative embodiment shown in FIG. 1, transalkylation effluent 12 and non-recycled portion 10b of alkylation effluent 10, comprising amounts of cumene obtained from transalkylation and alkylation, respectively, are distilled together in benzene column 300 to recover lower boiling benzene fraction 6. Benzene fraction 6, enriched in benzene relative to the combined feed to benzene column 300, namely transalkylation effluent 12 and non-recycled portion 10b of alkylation effluent 10, therefore comprises benzene that has not reacted in alkylation reaction zone 100 or transalkylation reaction zone 200 due to its presence in stoichiometric excess in these zones. Portions of benzene fraction 6 are recycled back to reaction zones 100, 200 after benzene fraction 6 combines with fresh benzene 8. Thus, recycle alkylation benzene 4 is introduced as an alkylation feedstock component, together with propylene 2, to alkylation reaction zone 100, while recycle transalkylation benzene 14 is introduced, to transalkylation reaction zone 200, as a transalkylation feedstock component, together with at least a portion of DIPB fraction 16 recovered from DIPB column 500 as a lower boiling fraction that is enriched in DIPB relative to the feed to this column.

Depending on the operation of DIPB column 500, and particularly the pressure used, DIPB fraction 16 may also contain triisopropylbenzene (TIPB) as an additional polyalkylated benzene that may be beneficially reacted in transalkylation reaction zone 200 to yield additional cumene. However, in order to recover TIPB in the lower boiling DIPB fraction 16 of DIPB column 500, subatmospheric (i.e., vacuum) pressure is normally required to avoid temperatures that cause thermal degradation of the components being fractionated. According to embodiments of the invention, therefore, DIPB column 500 recovers lower boiling DIPB fraction 16, containing some or all of the TIPB that is fed to this column, such that both DIPB and TIPB in this lower boiling DIPB fraction are fed to transalkylation reaction zone 200 to yield additional cumene. In this case, the fractionation in DIPB column 500 is generally carried out at subatmospheric pressure.

However, due to the high cumene selectivity that may be achieved as a result of reduced recycle ratios of the alkylation effluent, direct and/or indirect heat exchange strategies, and/or reduced benzene:propylene alkylation feedstock ratios, as discussed above, a greater degree of flexibility in the operation of DIPB column 500 is possible. In particular, as cumene selectivity in the alkylation reaction zone 100 increases, the yield of TIPB in this zone may decrease to such an extent that vacuum distillation to recover the reduced quantity of this compound together with DIPB in DIPB column 500 is no longer economically justifiable, compared to simply allowing this compound to be recovered in heavy byproduct 20 as a higher boiling fraction removed from DIPB column 500. In this case, the fractionation in DIPB column 500 may be carried out at atmospheric or superatmospheric pressure, rather than subatmospheric pressure to save costs associated with the more complex vacuum distillation. Fractionation at atmospheric pressure or above may be desirable, for example, when cumene selectivity in alkylation reaction zone 100 is at least about 88% (e.g., from about 88% to about 92%) by weight. In this case, DIPB fraction 16 contains substantially no TIPB (e.g., less than 0.4% by weight, and often less than 0.1% by weight). In general, operation at high cumene selectivity, as described herein, results in a yield loss, to TIPB and higher molecular weight compounds, based on net (i.e., fresh or make-up) benzene and propylene added to (i.e., consumed in) the process, of less than 0.5% by weight. At sufficiently high cumene selectivity, this is possible even in embodiments in which DIPB column 500 is operated at above atmospheric pressure, such that TIPB is removed in heavy byproduct 20 without being subjected to transalkylation to produce additional cumene.

Like alkylation reaction zone 100, transalkylation reaction zone 200 may comprise one or a plurality of catalyst beds. In embodiments discussed above in which distillation in DIPB column 500 is carried out at atmospheric pressure or above and lower boiling DIPB fraction 16 contains substantially no TIPB, one or more beds of transalkylation catalyst within transalkylation reaction zone 200 advantageously comprises beta zeolite. Beta zeolite, unlike other transalkylation catalysts, is highly shape selective in the transalkylation reaction, such that the highly alkylated compound, TIPB, is not produced to any appreciable extent. Consequently, recycle of TIPB to a steady-state concentration is not required in order to prevent a net production of TIPB. Moreover, compared to other transalkylation catalysts such as those comprising Y zeolite, transalkylation catalysts comprising beta zeolite can be used to obtain a much higher per-pass conversion level of polyalkylated benzene compounds (DIPB and TIPB), because ethylbenzene (EB) is also not produced appreciably as a byproduct. Therefore, if TIPB is limited in the feedstock to the transalkylation reaction zone 200, transalkylation conversion (i.e., the conversion of polyalkylated benzene compounds such as DIPB) in the presence of a transalkylation catalyst comprising beta zeolite is generally at least about 60%, but may be as high as, for example, in the range from about 80% to about 92%, by weight.

In contrast, in order to limit the EB content in the cumene product 24, a representative transalkylation conversion in the presence of a transalkylation catalyst comprising, for example, Y zeolite or UZM-8 zeolite, is generally in the range from about 40% to about 70%, and typically from about 50% to about 60%, by weight. These levels of transalkylation conversion are generally associated with embodiments of the invention, described above, in which TIPB is distilled together with DIPB in lower boiling DIPB fraction 16 recovered from DIPB column 500, in this case normally operated under vacuum pressure.

In addition to benzene fraction 6 recovered as a lower boiling fraction from benzene column 300, a higher boiling cumene-rich fraction 22, enriched in cumene (relative to the combined feed to benzene column 300, namely transalkylation effluent 12 and non-recycled portion 10b of alkylation effluent 10) is also obtained. Cumene-rich fraction 22 is distilled in cumene column 400 to recover cumene product 24 as a lower boiling fraction, and higher boiling byproduct fraction 26. Cumene product 24 is further enriched in cumene relative to cumene-rich fraction 22, and higher boiling byproduct fraction 26 is enriched DIPB and TIPB relative to cumene-rich fraction 22. Byproduct fraction 26 is fed to DIPB column 500, as discussed above, to recover lower boiling DIPB fraction 16 and higher boiling byproduct fraction 20.

According to the illustrative embodiment depicted in FIG. 1, transalkylation feedstock 18, the combination of recycle transalkylation benzene 14 and diisopropylbenzene fraction 16, flows through transalkylation catalyst bed(s) in transalkylation reaction zone 200 to provide transalkylation effluent 22 with an additional amount of cumene that is co-fed to benzene column 300 with cumene from recycled portion 10b of alkylation effluent. The cumene from both effluents 10b, 12 is recovered in the product recovery section. In the combined transalkylation feedstock 18, the molar ratio of benzene:polyalkylated benzene compounds (e.g., DIPB and TIPB, if present) is generally in the range from about 1:1 to 10:1, and often from about 2:1 to about 4:1. Also, the temperature of transalkylation feedstock 18 at the inlet of transalkylation reaction zone 200 is generally from about 100° C. (212° F.) to about 200° C. (392° F.). All or part of the heat required to attain a desired inlet temperature of transalkylation feedstock 18 may be supplied using a heat exchanger (not shown).

Overall aspects of the invention are directed to processes that exploit the unexpected findings, and particularly high cumene selectivity, associated with various process parameters and/or catalyst systems described herein. Embodiments of the invention therefore relate to methods for producing cumene from the alkylation of benzene with propylene, comprising flowing an alkylation feedstock comprising benzene and propylene to an alkylation reaction zone to convert propylene in the alkylation reaction zone with a selectivity of at least about 85% to cumene. Advantageously, one or more catalyst beds within the alkylation reaction zone may comprise UZM-8 zeolitic alkylation catalyst. Selectivity improvement may be obtained using a low alkylation effluent recycle ratio (e.g., less than about 3:1 by weight), which is the ratio of the flow rate of the recycled portion of the alkylation effluent to the flow rate of the alkylation feedstock (namely the combined flow rate of benzene- and propylene-containing feeds to the alkylation reaction zone) is less than about 3:1 by weight. In other embodiments, no alkylation effluent recycle is used. Due to the more limited, or non-existent, ability to quench the alkylation reaction zone using direct heat exchange with the recycled portion of the alkylation effluent, indirect heat exchange may be carried out according to embodiments of the invention by removing heat from between at least one pair of adjacent beds within the alkylation reaction zone. Further improvements in cumene selectivity may be realized in embodiments in which the benzene:propylene molar ratio in the alkylation feedstock is at most about 2.5, or even at most about 1.5. Yet further process advantages may be obtained at high cumene selectivity by carrying out a distillation, in the product recovery section, at atmospheric pressure or higher to separate byproduct DIPB overhead and remove byproduct TIPB in the bottoms with the heavy byproduct. This distillation may be combined with the use of a transalkylation catalyst comprising beta zeolite to provide further advantages in terms of conversion in the transalkylation reaction zone.

In view of the present disclosure, it will be seen that several advantages may be achieved and other advantageous results may be obtained. Numerous other embodiments will be apparent to those having skill in the art and knowledge gained from the present disclosure, and it will be appreciated that these embodiments do not depart from the scope of the present disclosure.

The following example is set forth as representative of the present invention. This example is not to be construed as limiting the scope of the invention as this and other equivalent embodiments will be apparent in view of the present disclosure and appended claims.

EXAMPLE 1

A pilot scale process utilizing an alkylation reaction zone, a transalkylation reaction zone, and a product recovery section was used to evaluate the effect of a number of process parameters on the selectivity to cumene, obtained from the alkylation of benzene with propylene. The alkylation reaction zone included three reactors in series containing alkylation catalyst. The following combinations, shown below in Table 1, of (i) molar ratio of benzene:propylene (B/P Ratio) in the combined alkylation feedstock to the alkylation reactors and (ii) weight ratio of alkylation effluent recycle:alkylation feedstock (Recycle Ratio) to the alkylation reactors were studied in different operating phases.

TABLE 1

B/P Ratios and Recycle Ratios Studied in Pilot Plant Cumene Production

| Phase | B/P Ratio | Recycle Ratio |
|---|---|---|
| 1 | 2 | 6 |
| 2 | 2 | 3 |
| 3 | 2 | 2 |
| 4 | 2 | 1 |
| 5 | 2 | 0.5 |
| 6 | 2.5 | 0.5 |
| 7 | 2.5 | 0 |

In each of the operating phases, the propylene weight hourly space velocity (WHSV) in the alkylation reactor was 0.72 hr$^{-1}$, the reactor pressure was 38 barg (550 psig), and the inlet temperature to each of the three alkylation reactors was controlled at 110° C. (230° F.), except for Phase 1, in which the reactor inlet temperature was controlled at 130° C. (266° F.). The catalyst used in the alkylation reactor was UZM-8HR, comprising UZM-8 zeolite having a framework Si/Al$_2$ molar ratio in the range of 27-33. Conditions in the transalkylation reactor were maintained constant for all phases.

Figure 2:
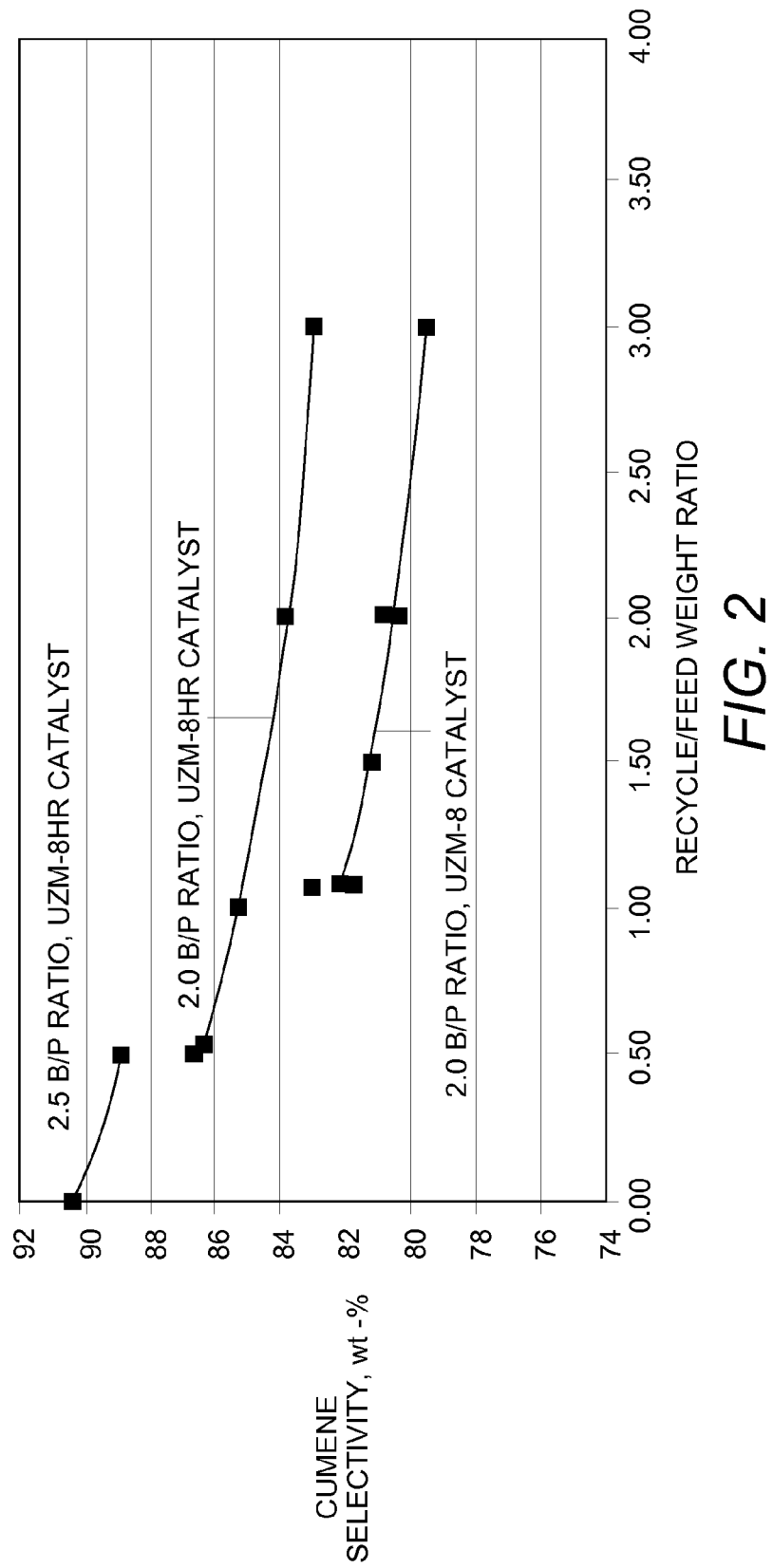
FIG. 2 is a graph of cumene selectivity in an alkylation reaction zone as a function of the alkylation effluent recycle ratio to this zone. Separate curves illustrate this relationship for an alkylation feedstock benzene to propylene (B/P) molar ratio of 2.0, used with UZM-8HR catalyst and a UZM-8 catalyst, and a B/P molar ratio of 2.5, used with UZM-8HR catalyst.

The cumene selectivity, or weight percent of cumene relative to the total weight of converted products including polyalkylated benzenes (DIPB and TIPB), was determined for each phase and analyzed as a function of the recycle ratio. The relationship is shown in FIG. 2, together with results obtained under the same conditions but with a UZM-8 catalyst comprising UZM-8 zeolite having a framework Si/Al$_2$ molar ratio in the range of 19-21. As illustrated in FIG. 2, operating at B/P ratio of 2.5 increased cumene selectivity from about 89% at a recycle ratio of 0.5, to slightly over 90% when the recycle flow was stopped altogether. Increasing the B/P ratio from 2.0 to 2.5 effectively shifted the cumene selectivity vs. recycle ratio curve higher by about 2%, while maintaining the same trend. The difference between these curves for UZM-8HR catalyst and UZM-8 catalyst at a B/P ratio of 2.0 was consistently about 3%.

Figure 3:
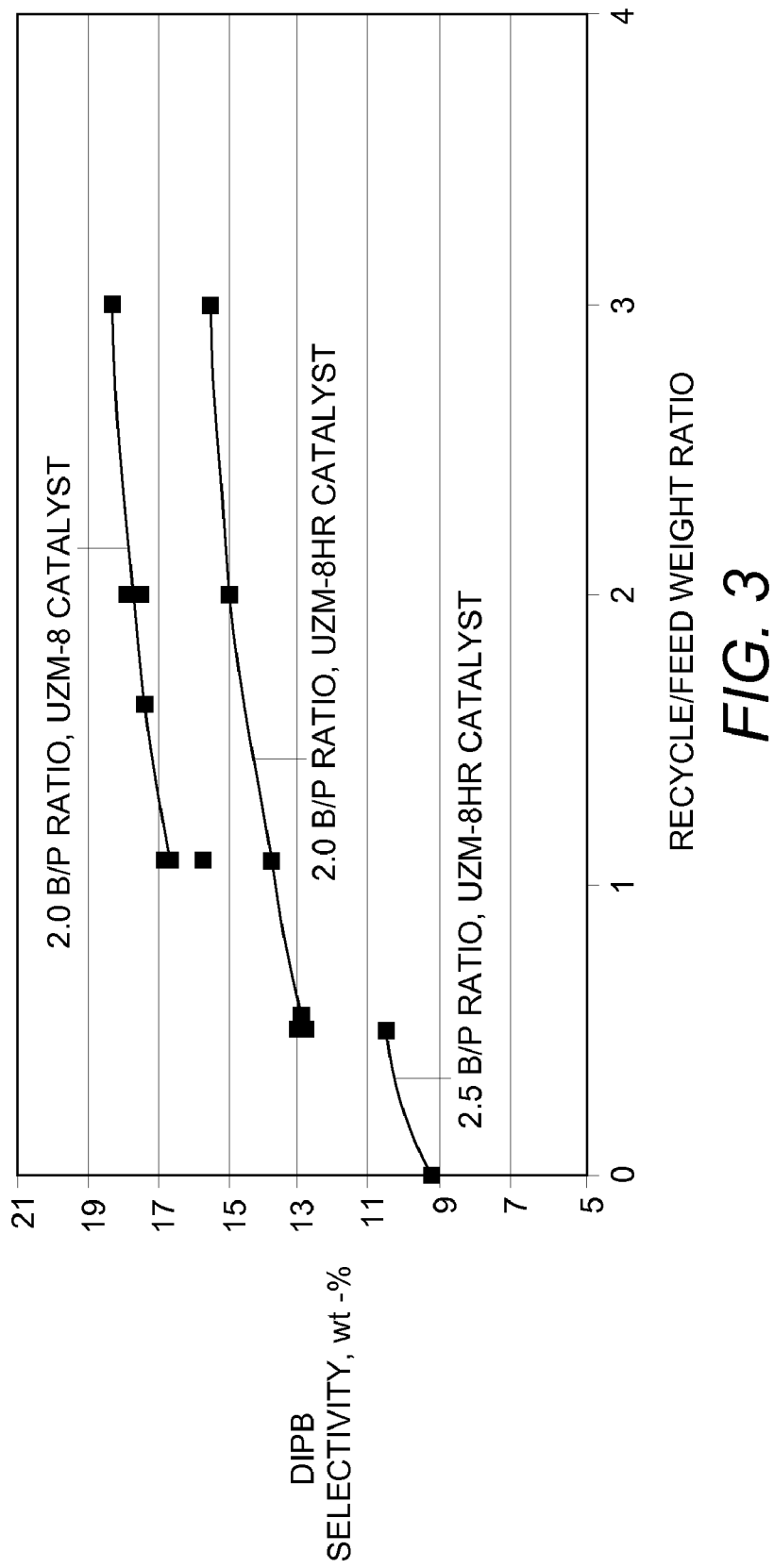
FIG. 3 is a graph of diisopropylbenzene (DIPB) selectivity in an alkylation reaction zone as a function of the alkylation effluent recycle ratio to this zone. Separate curves illustrate this relationship for an alkylation feedstock benzene to propylene (B/P) molar ratio of 2.0, used with UZM-8HR catalyst and a UZM-8 catalyst, and a B/P molar ratio of 2.5, used with UZM-8HR catalyst.

The DIPB selectivity, or weight percent of DIPB relative to the total weight of converted products, was determined for each phase and analyzed as a function of the recycle ratio. The relationship is shown in FIG. 3, again with results obtained under the same conditions but with UZM-8 catalyst. As illustrated in FIG. 3, decreasing the B/P ratio from 2.0 to 2.5 effectively shifted the DIPB selectivity vs. recycle ratio curve lower by about 1.75%, while maintaining the same trend. The difference between these curves for UZM-8HR catalyst and UZM-8 catalyst at a B/P ratio of 2.0 was consistently about 2.5%.

Figure 4:
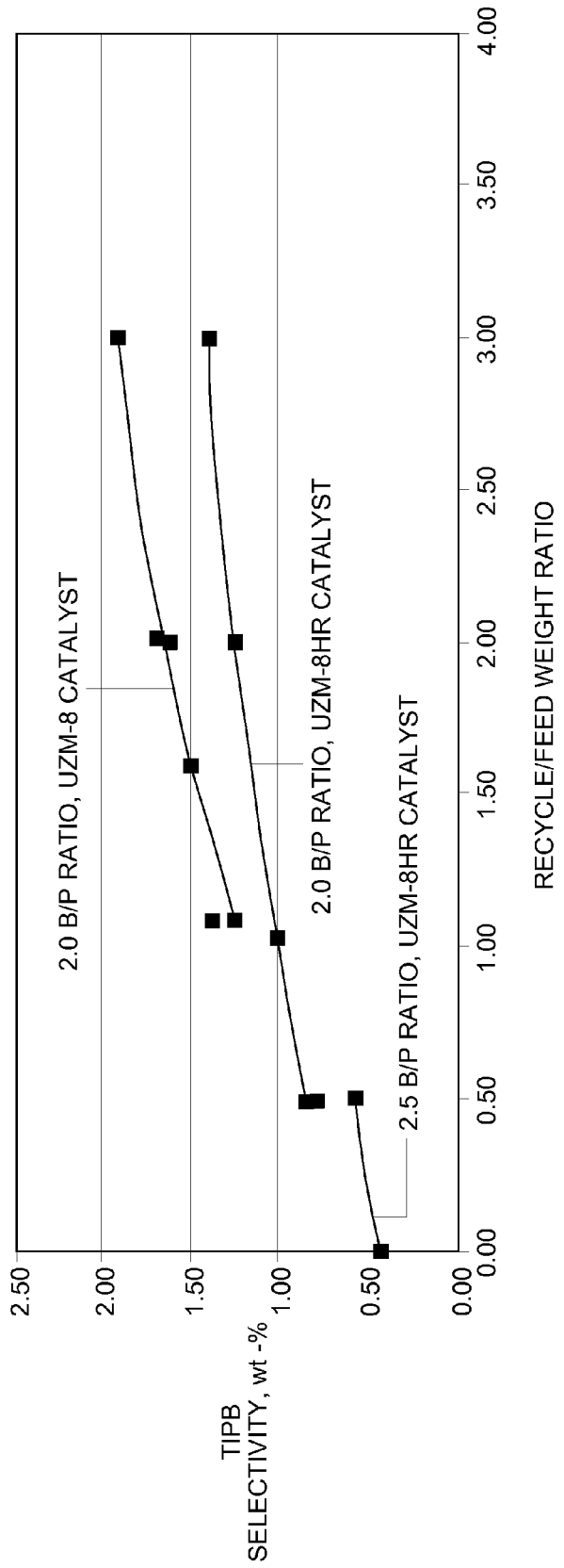
FIG. 4 is a graph of triisopropylbenzene (TIPB) selectivity in an alkylation reaction zone as a function of the alkylation effluent recycle ratio to this zone. Separate curves illustrate this relationship for an alkylation feedstock benzene to propylene (B/P) molar ratio of 2.0, used with UZM-8HR catalyst and a UZM-8 catalyst, and a B/P molar ratio of 2.5, used with UZM-8HR catalyst.

The TIPB selectivity, or weight percent of TIPB relative to the total weight of converted products, was determined for each phase and analyzed as a function of the recycle ratio. This relationship is shown in FIG. 4, again with results obtained under the same conditions but with a UZM-8 catalyst. As illustrated in FIG. 4, decreasing the B/P ratio from 2.0 to 2.5 effectively shifted the TIPB selectivity vs. recycle ratio curve lower. At this B/P ratio, the selectivity to TIPB was reduced to about 0.5% by weight or less. Compared to UZM-8 catalyst, the use of UZM-8HR catalyst decreased the selectivity to this byproduct at a 2.0 B/P ratio.

Using the UZM-8HR catalyst, the amount of byproduct normal-propylbenzene (NPB) in the alkylation effluent generally ranged from about 50 ppm to about 250 ppm based on the weight of cumene in this effluent. Under the conditions studied, an increasing production of NPB generally accompanied an increase in the average alkylation reaction zone temperature (or weighted average alkylation catalyst bed temperature). Likewise, an increasing production of byproduct butylbenzene generally accompanied an increase in the average alkylation reaction zone temperature, although increasing the B/P ratio had the effect of decreasing its production. The amount of butylbenzene in the alkylation effluent generally ranged from about 5 ppm to about 200 ppm, based on the weight of cumene in this effluent. The amount of byproduct ethylbenzene in the alkylation effluent was generally less than 20 ppm, based on the weight of cumene in this effluent, and this amount was relatively constant under all conditions tested. An increasing production of byproduct indenes generally accompanied an increase in the recycle ratio under the conditions tested. The amount of indenes in the alkylation effluent generally ranged from about 1000 to 2000 ppm, based on the weight of cumene in this effluent.

The reduction in recycle ratio from 3:1 to 0 had a dramatic effect on the temperature rise across each of the catalyst beds within the alkylation reaction zone. The temperature rise was about 17-25° C. (30-45° F.) at 3:1 recycle ratio, compared to 50-61° C. (90-111° F.) without any recycle. Therefore, the use of heat removal from the alkylation reaction zone by indirect heat exchange provides a practical alternative to direct heat exchange for reducing the temperature differential across the alkylation reaction zone when the alkylation effluent recycle flow rate is reduced or eliminated.

The invention claimed is:

1. A method for producing cumene from the alkylation of benzene with propylene, the method comprising:
    (a) flowing an alkylation feedstock comprising benzene and propylene to an alkylation reaction zone comprising at least three alkylation catalyst beds in series within a single alkylation reactor comprising UZM-8 zeolite having a framework $Si/Al_2$ molar ratio from about 27 to about 33, the heat is removed from between at least each of both pairs of adjacent beds of the at least three alkylation catalyst beds, and at a temperature difference across each of the alkylation catalyst beds is from about 15° C. (27° F.) to about 60° C. (108° F.), wherein the alkylation feedstock to the alkylation reaction zone is at a benzene : propylene molar ratio of at most about 2.5;
    (b) withdrawing from the alkylation reaction zone an alkylation effluent comprising cumene, wherein the propylene in the alkylation feedstock is converted in the alkylation reaction zone with a selectivity of at least about 85% to cumene; and
    (c) recycling a recycled portion of the alkylation effluent to the alkylation reaction zone, wherein a ratio of a flow rate of the recycled portion to a flow rate of the alkylation feedstock is less than about 0.5:1 by weight, wherein a flow of the recycled portion is divided among locations between at least each of both pairs of adjacent beds.

2. The method of claim 1, wherein the heat is removed by indirect heat exchange between an alkylation catalyst bed effluent and water to generate steam.

3. The method of claim 1, further comprising:
    (d) feeding (I) at least a non-recycled portion of the alkylation effluent, optionally following fractionation to remove light components, and (II) a transalkylation effluent, comprising an additional amount of cumene, to a product recovery section.

4. The method of claim 3, further comprising, in the product recovery section:
    (e) distilling the non-recycled portion of the alkylation effluent together with the transalkylation effluent to recover a lower boiling, benzene fraction and a higher boiling, cumene-rich fraction, and
    (f) distilling the cumene-rich fraction to recover a lower boiling, cumene product and a higher boiling, byproduct fraction enriched in combined diisopropylbenzene and triisopropylbenzene, and
    (g) distilling the byproduct fraction to recover a lower boiling, diisopropylbenzene fraction and a higher boiling heavy byproduct,
    wherein step (g) is carried out above atmospheric pressure.

5. The method of claim 4, wherein the transalkylation effluent is withdrawn from a transalkylation reaction zone comprising a zeolitic transalkylation catalyst comprising beta zeolite, and a transalkylation feedstock comprising at least a portion of the benzene fraction and at least a portion of the diisopropylbenzene fraction recovered in step (d) are contacted with the zeolitic transalkylation catalyst in the transalkylation reaction zone.

6. The method of claim 5, wherein a conversion of diisopropylbenzene in the transalkylation reaction zone is at least about 80%.

* * * * *